United States Patent [19]

Shuber

[11] Patent Number: 5,849,483

[45] Date of Patent: *Dec. 15, 1998

[54] HIGH THROUGHPUT SCREENING METHOD FOR SEQUENCES OR GENETIC ALTERATIONS IN NUCLEIC ACIDS

[75] Inventor: Anthony P. Shuber, Milford, Mass.

[73] Assignee: IG Laboratories, Inc., Framingham, Mass.

[*] Notice: The term of this patent shall not extend beyond the expiration date of Pat. No. 5,589,330.

[21] Appl. No.: 485,885

[22] Filed: Jun. 7, 1995

Related U.S. Application Data

[63] Continuation-in-part of Ser. No. 281,940, Jul. 28, 1994, Pat. No. 5,589,330.

[51] Int. Cl.$^6$ .............................. C12Q 1/68; C12P 19/34
[52] U.S. Cl. .................................... 435/5; 435/6; 435/91.2
[58] Field of Search ................................. 435/5, 6, 91.1, 435/91.2; 935/78

[56] References Cited

U.S. PATENT DOCUMENTS

| 5,434,049 | 7/1995 | Okano et al. | 435/6 |
| 5,470,705 | 11/1995 | Grossman et al. | 435/6 |
| 5,514,543 | 5/1996 | Grossman et al. | 435/6 |

OTHER PUBLICATIONS

Shuber et al., et al., *Hum. Mol. Genet.* 2(2), 153–158 (1993).
Verlaan–de Vries et al., *Gene* 50, 313–320 (1986).

*Primary Examiner*—Kenneth R. Horlick
*Attorney, Agent, or Firm*—Darby & Darby

[57] ABSTRACT

A high-throughput method for screening nucleic acid samples to identify target sequences or one or more genetic alterations in target sequences present in the nucleic acid samples. Methods of identifying target nucleic acid sequences in patient samples, and of identifying randomly permuted alterations in nucleic acid sequences of interest are also included.

25 Claims, 5 Drawing Sheets

A panel of different patient samples hybridized with pools of mutation specific oligonucelotides Positive screening result Identification of specific mutations

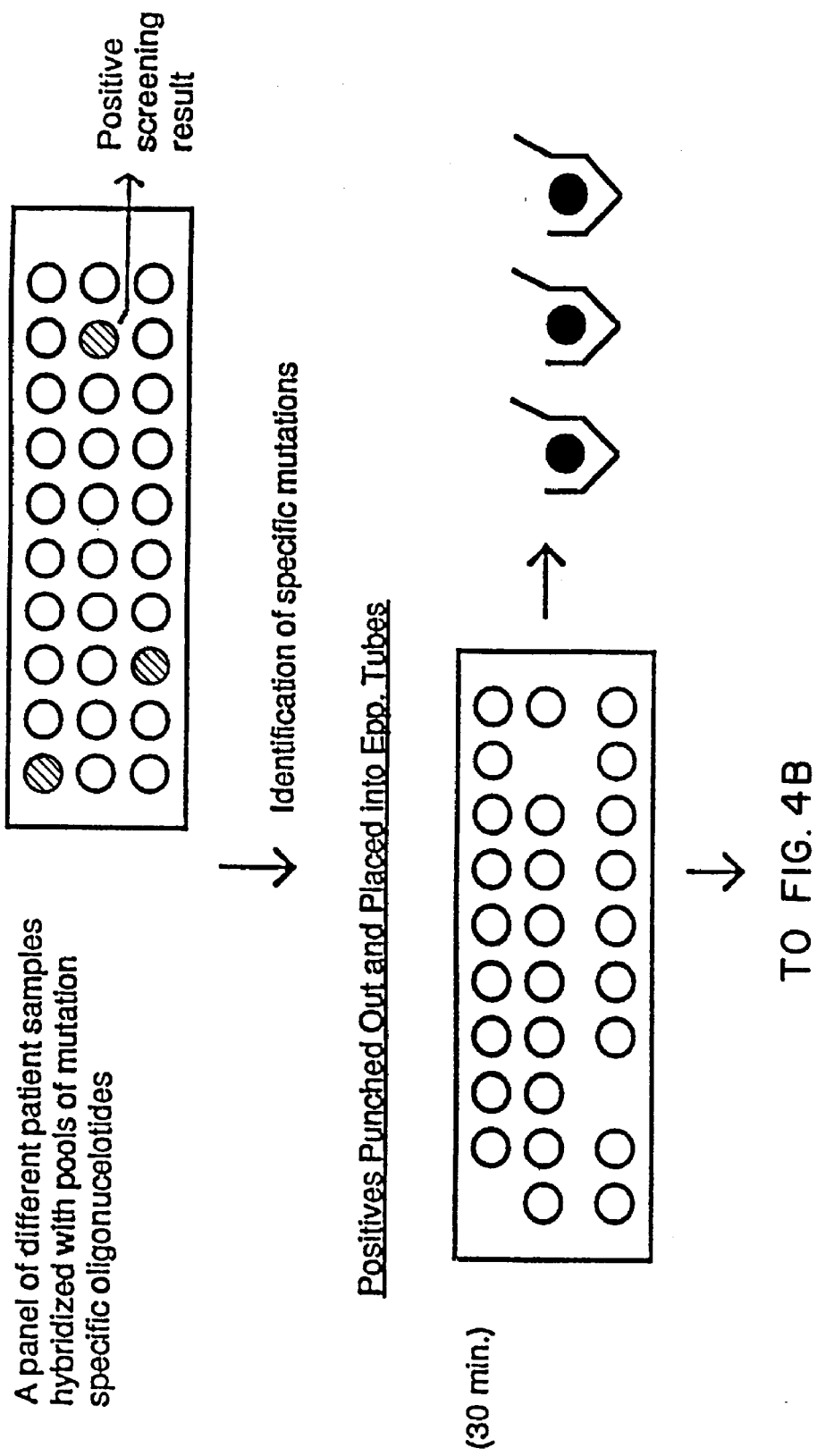

FIG. 4B

HIGH THROUGHPUT SCREENING METHOD FOR SEQUENCES OR GENETIC ALTERATIONS IN NUCLEIC ACIDS

This application is a continuation-in-part of patent application Ser. No. 08/281,940, filed on Jul. 28, 1994, U.S. Pat. No. 5,589,330.

FIELD OF THE INVENTION

This invention pertains to high throughput screening of nucleic acid samples in order to determine one or more genetic alterations in those samples. This invention also pertains to the identification of specific disease-causing nucleic acid sequences in mammals. The methods of the present invention can be used to identify genetic polymorphisms, to determine the molecular basis for genetic diseases, and to provide carrier and prenatal diagnosis for genetic counseling. Furthermore, the invention pertains to specific high-resolution identification of disease-causing microorganisms in mammals.

BACKGROUND OF THE INVENTION

The ability to identify and detect differences in nucleic acid sequences and, more particularly in DNA sequences (i.e. mutations) is central to the diagnosis of genetic diseases and to the identification of clinically significant variants of disease-causing microorganisms. One method for the molecular analysis of genetic variation involves the detection of restriction fragment length polymorphisms (RFLPs) using the Southern blotting technique (Southern, E. M., *J. Mol. Biol.*, 98:503–517, 1975; Kan et al., *Nature*, 313:369–374, 1978; Wyman et al. *Proc. Natl. Acad. Sci., USA*, 77:6754–6758, 1980). Since this approach is relatively cumbersome, new methods have been developed, some of which are based on the polymerase chain reaction (PCR). These include: RFLP analysis using PCR (Chehab et al., *Nature*, 329:293–294, 1987; Rommens et al., *Am. J. Hum. Genet:.*, 46:395–396, 1990), the creation of artificial RFLPs using primer-specified restriction-site modification (Haliassos et al., *Nucleic Acids Research*, 17:3606, 1989), and hybridization to allele-specific oligonucleotides (ASOs) (Saiki et al., *Nature*, 324:163–166, 1986).

These methods are limited in their applicability to complex mutational analysis. For example, in cystic fibrosis, a recessive disorder affecting 1 in 2000–2500 live births in the United States, more than 225 presumed disease-causing mutations have been identified. Furthermore, multiple mutations may be present in a single affected individual, and may be spaced within a few base pairs of each other. These phenomena present unique difficulties in designing clinical screening methods that can accommodate large numbers of sample DNAs.

U.S. patent application Ser. No. 08/308,638, filed Sep. 19, 1994, U.S. Pat. No. 5,633,134, Shuber et al., *Human Molecular Genetics*, 2:153–158 (1993), and the present invention disclose a method that allows the simultaneous hybridization of multiple oligonucleotide probes to a single target DNA sample. By including in the hybridization reaction an agent that eliminates the disparities in melting temperatures of hybrids formed between synthetic oligonucleotides and target DNA, it is possible in a single test to screen a DNA sample for the presence of different mutations. Typically, more than 50 ASOs can be pooled and hybridized to target DNA; in a second step, ASOs from a pool giving a positive result are individually hybridized to the same DNA.

This methodology is, however, limited by the necessity of performing subsequent multiple individual hybridizations to identify the relevant ASO from the pool. Thus, there is a need in the art for relatively low cost methods that allow the efficient screening of large numbers of nucleic acid samples and, particularly DNA samples for genetic variation and the rapid identification of the sequences and variant sequences.

SUMMARY OF THE INVENTION

The present invention encompasses high-throughput methods for detecting and identifying sequences or genetic alterations (defined as nucleotide additions, deletions, or substitutions) in a large number of nucleic acid samples, which is achieved by: immobilizing a plurality of the nucleic acid samples on a support; providing a multiplicity of purine and pyrimidine containing polymers at substantially the same time; removing the purine and pyrimidine containing polymers that do not hybridize to the immobilized samples; separating the hybridized purine and pyrimidine containing polymers from the immobilized samples; identifying the separated purine and pyrimidine containing polymers; wherein the identification of the separated purine and pyrimidine containing polymers identifies the nucleic acid sequence or one or more genetic alterations. The separated purine and pyrimidine polymers can be identified, for example, by sequencing, direct labeling, indirect labeling and labeling with a unique length marker.

In accordance with the present invention, both the target nucleic acid sequence and/or the separated purine and pyrimidine containing polymers may be amplified using the polymerase chain reaction (PCR) to facilitate detection and identification. Importantly, hybridizations are carried out under conditions that minimize the differences in melting temperature of hybrids formed between different purine and pyrimidine containing polymers and the target nucleic acid sequence.

Figure 2:
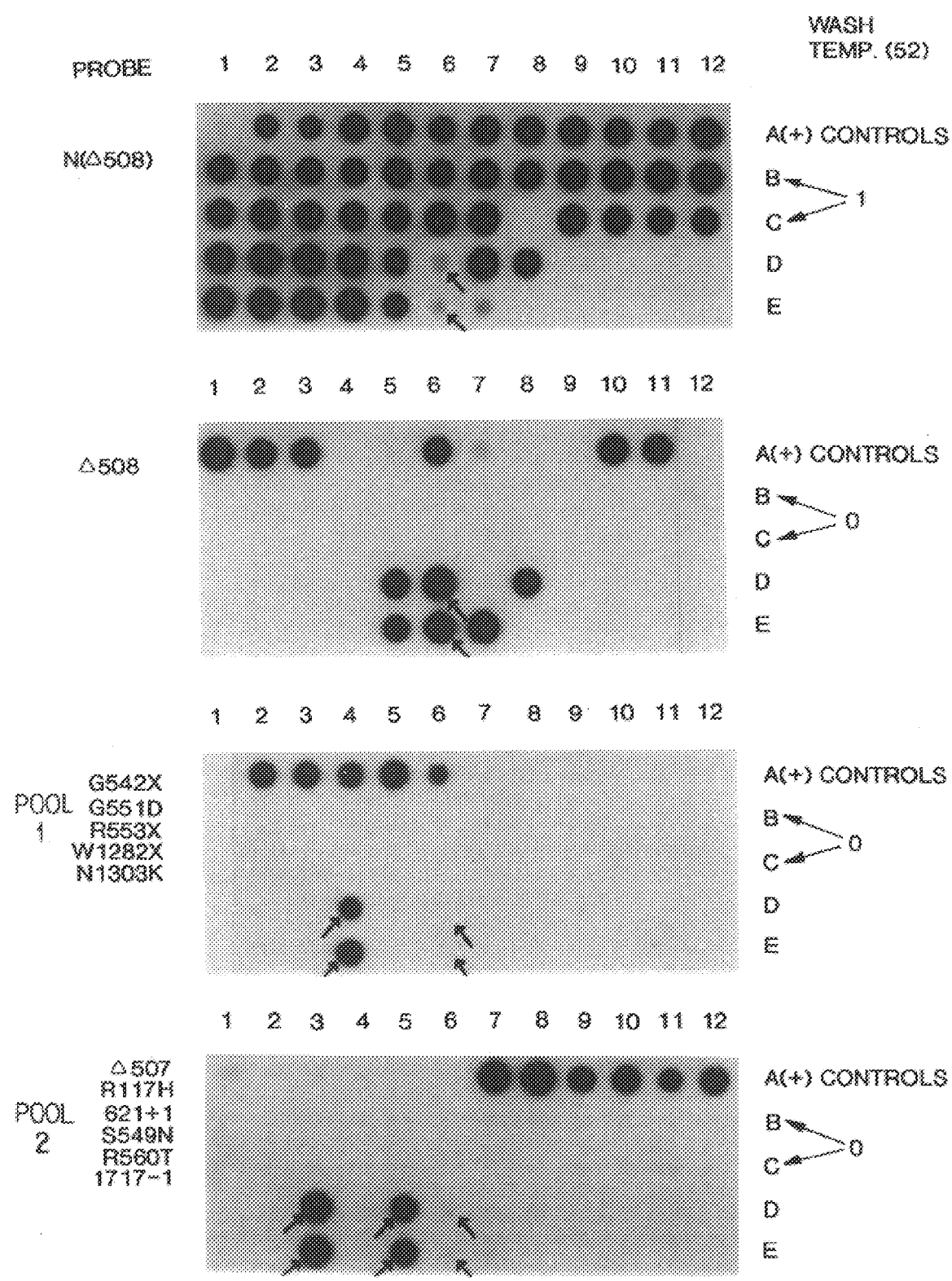
FIG. 2 shows autoradiographic results obtained from hybridizing four identical filters containing human genomic DNA with $^{32}$P-labeled ASOs specific for different alleles of the cystic fibrosis transmembrane regulator (CFTR) gene. The ASOs used in each hybridization are identified on the left of each filter. The lanes marked A contain positive control DNA samples. Rows B–E contain patient samples analyzed in duplicate, with the exception of 8C (amplification failure on duplicate sample), and D7, D8 and E7 (positive controls).

Pool 2, lanes 1 and 2 contains sample 3, lanes D and E from FIG. 2. Lanes 3 and 4 contain sample 5, lanes D and E from FIG. 2.

Figure 4B:
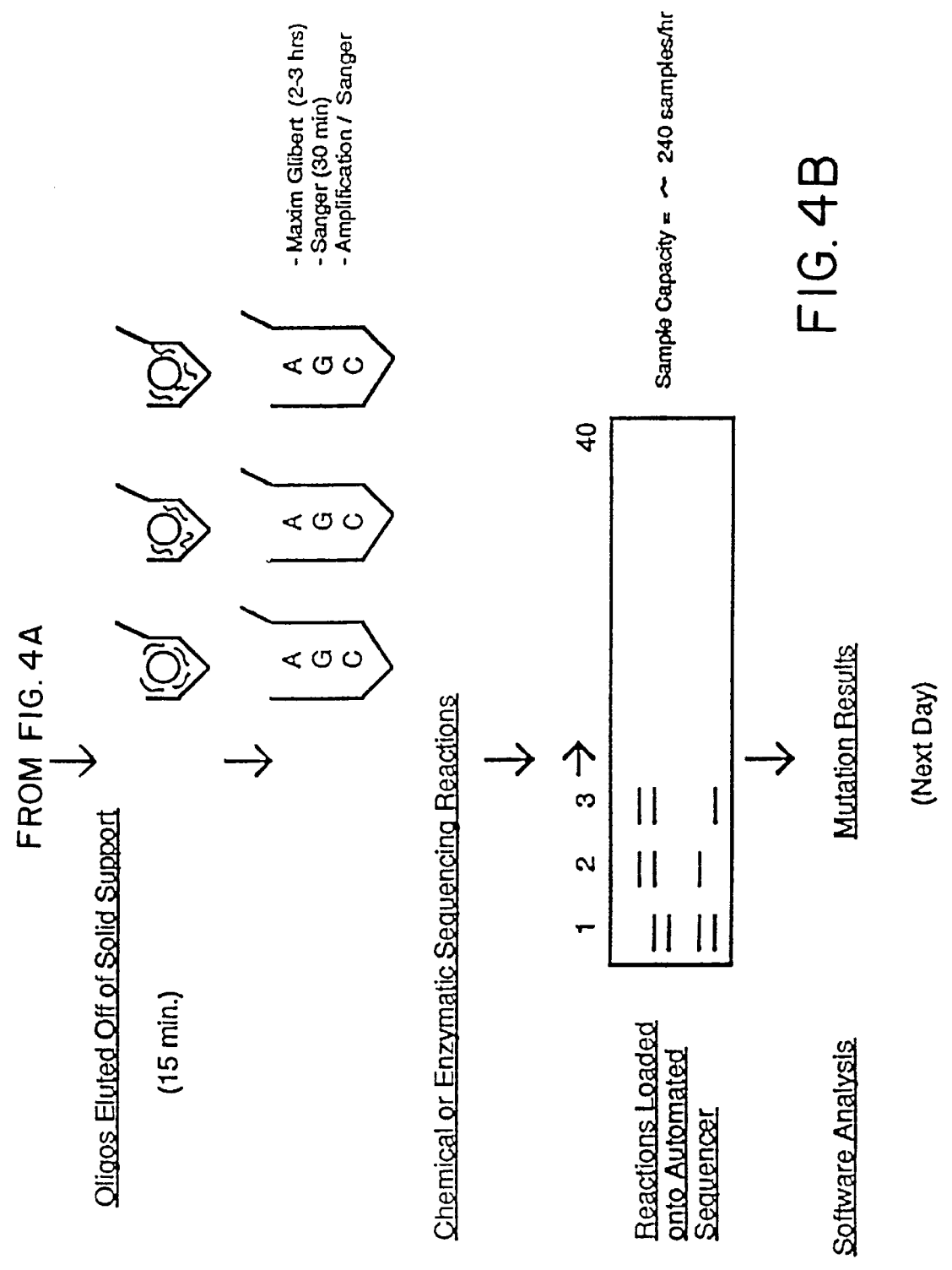

FIG. 4A–B shows a schematic representation of the methods of the present invention.

DETAILED DESCRIPTION OF THE INVENTION

All patent applications, patents, and literature references cited in this specification are hereby incorporated by reference in their entirety. In case of conflict, the present description, including definitions, will control.

Definitions

1. An "allele-specific oligonucleotide" (ASO) as defined herein is an oligonucleotide having a sequence that is identical or almost identical to a known nucleic acid portion. Often, an ASO contains a small change relative to the prevalent "wild type" sequence. This change may comprise addition, deletion, or substitution of one or more nucleotides. ASOs can be designed to identify any addition, deletion, or substitution, as long as the nucleic acid sequence is known.

2. A "variant" sequence as used herein encompasses a nucleic acid sequence that differs from a known sequence by the addition, deletion, or substitution of one or more nucleotides.

3. "Amplification" of nucleic acid sequence as used herein denotes the use of polymerase chain reaction (PCR) or other amplification methods to increase the concentration of a particular nucleic acid sequence within a mixture of nucleic acid sequences. For a description of PCR see Saiki et al., *Science* 239:487 (1988).

4. "Chemical sequencing" denotes methods such as that of Maxim and Gilbert (Maxim-Gilbert sequencing, Maxam and Gilbert, 1977, *Proc. Natl. Acad. Sci., USA* 74:560), in which nucleic acids are randomly cleaved using individual base-specific reactions.

5. "Enzymatic sequencing" denotes methods such as that of Sanger (Sanger et al., 1977, *Proc. Natl. Acad. Sci., USA* 74:5463), in which a single-stranded DNA is copied and randomly terminated using DNA polymerase.

6. In this specification, the terms "bound" and "hybridized" are used interchangeably to denote the formation of nucleic acid to purine and pyrimidine containing polymer duplexes. The term "affinity purified" denotes purification using hybridization.

7. "High-throughput" denotes the ability to simultaneously process and screen a large number of nucleic acid samples (e.g., in excess of 50 or 100 nucleic acid samples) and a large number of target sequences within those samples in a rapid and economical manner.

8. "Purine and pyrimidine containing polymers" is meant to include DNA, RNA and other compounds that are capable of Watson-Crick base pairing and, which do not necessarily carry a sugar phosphate backbone such as, for example, PNA. See, *J. Am. Chem. Soc.* 114:1895–97 (1992).

The present invention encompasses a high-throughput method for screening nucleic acid samples for target sequences or sequence alterations and more particularly, for specific sequences in DNA isolated from a patient. The method is applicable when one or more genes or genetic loci are targets of interest. It will also be appreciated that this method allows for rapid and economical screening of a large number of nucleic acid samples for target sequences of interest.

In one embodiment, the specific nucleic acid sequence comprises a portion of a nucleic acid, a particular gene or a genetic locus in a genomic DNA known to be involved in a pathological condition or syndrome. Non-limiting examples include cystic fibrosis, sickle-cell anemia, β-thalassemia, and Gaucher's disease.

In another embodiment, the specific nucleic acid sequence comprises part of a particular gene or genetic locus that may not be known to be linked to a particular disease, but in which polymorphism is known or suspected.

In yet another embodiment, the specific nucleic acid sequence comprises part of a foreign genetic sequence e.g. the genome of an invading microorganism. Non-limiting examples include bacteria and their phages, viruses, fungi, protozoa, and the like. The present methods are particularly applicable when it is desired to distinguish between different variants or strains of a microorganism in order to choose appropriate therapeutic interventions.

In accordance with the present invention, the target nucleic acid represents a sample of nucleic acid isolated from a patient. This nucleic acid may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include, for example, blood, urine, cerebrospinal fluids and tissue exudates at the site of infection or inflammation. Nucleic acids can be extracted from the cell source or body fluid using any of the numerous methods that are standard in the art. It will be understood that the particular method used to extract the nucleic acid will depend on the nature of the source. The minimum amount of DNA, for example, that can be extracted for use in a preferred form of the present invention is about 5 pg (corresponding to about 1 cell equivalent of a genome size of $4 \times 10^9$ base pairs).

Once extracted, the target nucleic acid may be employed in the present invention without further manipulation. Alternatively, one or more specific nucleic acid regions present in the target nucleic acid may be amplified, for example, by PCR. In this case, the amplified regions are specified by the choice of particular flanking sequences for use as primers. Amplification at this step provides the advantage of increasing the concentration of specific nucleic acid sequences within the target nucleic acid sequence population. The length of nucleic acid sequence that can be amplified ranges from 80 bp to up to 30 kbp (Saiki et al., 1988, *Science,* 239:487).

In one embodiment, the target nucleic acid, with or without prior amplification of particular sequences, is bound to a solid-phase or semi-solid phase matrix. This allows for the simultaneous processing and screening of a large number of nucleic acid samples from different sources. Non-limiting examples of matrices suitable for use in the present invention include nitrocellulose or nylon filters, glass beads, magnetic beads coated with agents for affinity capture, treated or untreated microtiter plates, polymer gels, agarose and the like. It will be understood by a skilled practitioner that the method by which the target nucleic acid is bound to the matrix will depend on the particular matrix used. For example, binding to nitrocellulose can be achieved by simple adsorption of nucleic acid to the filter, followed by baking the filter at 75°–80° C. under vacuum for 15 min-2 h. Alternatively, charged nylon membranes can be used that do not require any further treatment of the bound nucleic acid. Beads and microtiter plates that are coated with avidin can be used to bind target nucleic acid that has had biotin attached (via e.g., the use of biotin-conjugated PCR primers). In addition, antibodies can be used to attach target nucleic acid to any of the above solid supports by coating the surfaces with the antibodies and incorporating an antibody-specific hapten into the target nucleic acid.

In practicing the present invention, the untreated or amplified target nucleic acid, preferably bound to a solid-phase or semi-solid phase matrix, is incubated with a mixture of purine and pyrimidine containing polymers (hereinafter also referred to as "polymer" or "polymers"). These polymers can be, preferably, allele-specific oligonucleotides (ASOs). 10–200 polymers can be pooled for a single hybridization, preferably 50–100 and most preferably 50. The length of individual polymers may be 16–25 nucleotides, preferably 17 nucleotides in length.

The purine and pyrimidine containing polymers may be synthesized chemically by methods that are standard in the art, e.g., using commercially available automated synthesizers. These polymers may then be radioactively labeled (e.g., end-labeled with $^{32}P$ using polynucleotide kinase) or conjugated to other commonly used "tags" or reporter molecules. For example, fluorochromes (such as FITC or rhodamine), enzymes (such as alkaline phosphatase), biotin, or other well-known labelling compounds may be attached directly or indirectly. Furthermore, using standard methods, a large number of randomly permuted polymers can be synthesized in a single reaction. As detailed below, the present invention does not require that individual hybridizing sequences be determined prior to the hybridization. Rather, the sequence of bound polymers can be determined in a later step.

As described in U.S. patent application Ser. No. 07/957,205 (filed Oct. 6, 1992, abandoned) and in Shuber et al., 1993, *Human Molecular Genetics,* 2:153–158, the hybridization reaction is performed under conditions in which polymers such as ASOs containing different sequences hybridize to their complementary DNA with equivalent strength. This is achieved by: 1) employing ASOs of equivalent length; and 2) including in the hybridization mixture appropriate concentrations of one or more agents that eliminate the disparity in melting temperatures among ASOs of identical length but different guanosine+cytosine (G+C) compositions. Agents that may be used for this purpose include without limitation quaternary ammonium compounds such as tetramethylammonium chloride (TMAC).

TMAC acts through a non-specific salt effect to reducing hydrogen-bonding energies between G–C base pairs. At the same time, it binds specifically to A–T pairs and increases the thermal stability of these bonds. These opposing influences have the effect of reducing the difference in bonding energy between the triple-hydrogen bonded G–C based pair and the double-bonded A–T pair. One consequence, as noted above, is that the melting temperature of nucleic acid to nucleic acid hybrids formed in the presence of TMAC is solely a function of the length of the hybrid. A second consequence is an increase in the slope of the melting curve for each probe. Together these effects allow the stringency of hybridization to be increased to the point that single-base differences can be resolved, and non-specific hybridization minimized (Wood et al., 1985, *Proc. Natl. Acad. Sci., USA* 82:1585).

It will be apparent to those skilled in the art that any agent that exhibits these properties can be used in practicing the present invention. Such agents can be easily identified by determining melting curves for different test oligonucleotides in the presence and absence of increasing concentrations of the agent. This can be achieved by attaching a target nucleic acid to a solid matrix such as a nylon filter, individually hybridizing radiolabeled oligonucleotides of identical length but different G+C compositions to the filter, washing the filter at increasing temperatures, and measuring the relative amount of radiolabeled probe bound to the filter at each temperature. An agent that, when present in the hybridization and washing steps described above, results in approximately superimposable and steep melting curves for the different oligonucleotides may be used.

In practicing the present invention, the target nucleic acid and polymers are incubated for sufficient time and under appropriate conditions to achieve maximal specific hybridization and minimal non-specific i.e., background hybridization. The conditions to be considered include the concentration of each polymer, the temperature of hybridization, the salt concentration, and the presence or absence of unrelated nucleic acid. It will further be appreciated that the polymers can be broken into at least two groupings, each grouping containing a sufficient number of polymers to allow for hybridization. For example, it may be preferred to divide the total number of polymers of a pool to be hybridized to the nucleic acid samples into groupings of about 50 polymers. Each group of polymers can be hybridized to the nucleic acid immobilized on the support in a sequential manner, but the polymers comprising each group can be hybridized to the nucleic acid at substantially the same time. Additionally, immobilized nucleic acid samples may be hybridized to at least one pool of polymers, the identity of the hybridizing polymers determined, and then the nucleic acid samples hybridized again with the same or different polymer pools.

The concentration of each purine and pyrimidine containing polymer may range from 0.025 to 0.2 pmol per ml of hybridization solution. When polymers of known sequence are used, the optimal concentration for each polymer is determined by test hybridizations in which the signal-to-noise ratio (i.e., specific vs. non-specific binding) of each polymer is measured at increasing concentrations of labeled polymer. To further reduce background hybridization, oligonucleotides containing the non-variant unlabeled (i.e., wild-type) sequence may be included in the reaction mixture at a concentration equivalent to 1 to 100 times the concentration of the labeled polymer.

The temperature for hybridization is optimized to be as high as possible for the length of the polymers being used. This can be determined empirically, using the melting curve determination procedure described above. It will be understood by skilled practitioners that determination of optimal time, temperature, polymer concentration and salt concentration should be done in concert.

Following hybridization, unbound polymers are removed by washing the matrix-bound nucleic acid in a solution containing TMAC or similar compounds, under conditions that preserve perfectly matched nucleic acid to polymer hybrids. Washing conditions such as temperature, nature and concentration of salts, and time of washing, are determined empirically as described above. At this stage, the presence of bound polymers may be determined before proceeding to the separation step (see below). Different methods for detection will depend upon the label or tag incorporated into the polymers. For example, radioactively labeled or chemiluminescent polymers that have bound to the target nucleic acid can be detected by exposure of the filter to X-ray film. Alternatively, polymers containing a fluorescent label can be detected by excitation with a laser or lamp-based system at the specific absorption wavelength of the fluorescent reporter. Still further, polymers can each carry, in addition to the probe sequence, a molecular weight modifying entity (MWME) which is unique for each member of the polymer pool. The MWME does not participate in the hybridization reaction but allows direct identification of the separated polymer by determination of the relative molecular weight by any number of methods. Other methods for detection and identification are described below.

In a subsequent step, the bound polymers are separated from the matrix-bound target nucleic acid. Separation may be accomplished by any means known in the art that destabilizes nucleic acid to polymer hybrids, i.e., lowering salt, raising temperature, exposure to formamide, alkali, etc. In a preferred embodiment, the bound polymers are separated by incubating the target nucleic acid to polymer complexes in water, and heating the reaction above the melting temperature of the nucleic acid to polymer hybrids. This obviates the need for further treatment or purification of the separated polymers.

According to this invention, the separated polymers can be identified by a number of different methods that will be readily appreciated by those of skill in the art. For example, target sequences and different genetic alterations can be identified by using polymers of unique sequences. By sequencing the polymer, it is possible to correspondingly identify the target sequence or genetic alterations in the nucleic acid samples.

The polymers can also be identified by directly labeling them with a unique reporter that provides a detectable signal. Polymers that are direct labeled can be detected using radioactivity, fluorescence, colorimetry, chemiluminescence, and electrochemiluminescence, and the like. Suitable labels can include fluorophores, chromophores, radioactive atoms (such as $^3P$ and $^{125}I$), electron dense reagents, and enzymes detectable by their activity. See L.Kricka, Nonisotopic DNA Probe Techniques, Chapters 1 and 2, Academic Press, 1992 (hereinafter "Kricka").

In addition to direct labeling of polymers, indirect labeling may also be used. There are many binding pairs which are known in the art for indirect labeling including, for example, biotin-avidin, biotin-streptavidin, hapten-antihapten antibody, sugar-lectin, and the like. When used with the instant invention, one member of a binding pair is attached to the polymer and the other member of the binding pair is directly labeled as described above. Subsequent to hybridization, the polymers that are bound to target nucleic acid sequences may be identified by incubation with the labeled member, and subsequent detection of the binding pair-label complex. See Bioconjugate Chemistry, 1(3): 165–187 (1990), Kricka, Chapters 1 and 2.

The polymers can still further be identified by using unique length markers. That is, by providing polymers having components that contribute a predetermined and unique molecular weight to each individual polymer, in addition to the portions that participate in hydrogen bonding interactions with target nucleic acids, it is possible to identify the individual polymer by molecular weight. See, e.g., Nucleic Acids Res. 22 (21):4527–4534 (1994).

Still further, separated polymers can be identified by use of hybridization arrays. In such arrays, purine and pyrimidine containing polymers of predetermined sequence are immobilized at discrete locations on a solid or semi-solid support. When used with the instant invention, the sequence of each immobilized polymer comprising the array is complementary to the sequence of a member of the polymer pool. Members of the polymer pool that hybridize with target nucleic acids can be identified after separation from target nucleic acids by rehybridization with immobilized polymers forming the array. The identity of the polymer is determined by the location of hybridization on the array. See, for example, U.S. Pat. No. 5,202,231 and WO 8910977.

Other permutations and possibilities will be readily apparent to those of ordinary skill in the art, and are considered as equivalents within the scope of the instant invention.

More particularly, in one embodiment, the separated polymer is directly subjected to sequencing, using a chemical method standard in the art (e.g., Maxim-Gilbert sequencing, Maxam and Gilbert, 1977, Proc. Natl. Acad. Sci., USA 74:560). This method is particularly applicable when randomly permuted mixtures of polymers are used.

In another embodiment, the separated polymers are identified by enzymatic DNA sequencing (Sanger et al., 1977, Proc. Natl. Acad. Sci., USA 74:5463). In this case, oligonucleotides are synthesized that contain sequences complementary to the polymers and additional predetermined co-linear sequences that act as sequence "tags" (see Example 4 below). Separation of the polymers from the target nucleic acid is performed in the presence of a mixture of these complementary, "tagged" oligonucleotides. When incubated under Sanger sequencing conditions (see e.g., Example 5 below), the separated polymers hybridize to their complementary sequences and act as primers for the sequencing reaction. Determination of the resulting primed sequence "tag" then identifies the polymer(s) present in the reaction.

In a further embodiment, the separated polymers are incubated with complementary oligonucleotides that may contain universal primer sequences and/or a sequencing primer sequence with or without an additional "tag" sequence (see Example 4 below). In both cases, initial hybridization of a polymer to its complementary oligonucleotide allows the polymer to serve as the initial primer in a single extension reaction. In one case, the extension product is then used directly as template in a cycle sequencing reaction. Cycle sequencing of the extension products results in amplification of the sequencing products. In designing the complementary oligonucleotides, the sequencing primer is oriented so that sequencing proceeds through the polymer itself, or, alternatively, through the "tag" sequence.

In the second case, the extension product includes a universal primer sequence and a sequencing primer sequence. This extension product is then added to a linear PCR reaction in the presence of universal primer. The oligonucleotides containing complementary sequences to bound polymers are therefore selectively amplified. In a second step, these amplified sequences are subjected to Sanger sequencing, using the built-in sequencing primer sequence. In this case, the sequencing primer is placed immediately upstream of a "tag" sequence as above. Thus, determination of the "tag" sequence will identify the colinear polymer sequence.

In practicing the present invention, it is not necessary to determine the entire sequence of the polymer or of the complementary tagged oligonucleotide. It is contemplated that 1, 2, or 3 sequencing reactions (instead of the four needed to obtain a complete sequence) will be effective in producing characteristic patterns (similar to "bar codes") to allow the immediate identification of individual polymers. This approach is applicable to manual sequencing methods using radioactively labeled polymers, which produce analog or digitized autoradiograms, as well as to automated sequencing methods using non-radioactive reporter molecules, which produce digitized patterns. In either case, comparisons to an established data base can be performed electronically. Thus, by reducing the number of required sequencing reactions, the methods of the present invention facilitate the economical analysis of multiple samples, and of multiple nucleic acid sequences or genetic alterations within each sample.

The present invention accommodates the simultaneous screening of a large number of potential polymers in a single reaction. In practice, the actual number of polymers that are pooled for simultaneous hybridization is determined according to the diagnostic need. For example, in cystic fibrosis (CF), one particular mutation (Δ508) accounts for more than 70% of CF cases. Thus, a preliminary hybridization with a labeled or tagged Δ508-specific polymer according to the present methods, followed by detection of the bound polymer, will identify and eliminate Δ508 alleles. In a second ("phase two") hybridization, a large number of polymers encoding other, less frequent, CF alleles is performed, followed by separation and sequencing as described above.

In other clinical situations, however, a single mutation that appears with as high a frequency as the Δ508 mutation in CF does not exist. Therefore, pools of polymers are determined only by the number of independent hybridizations that would be needed in a phase two analysis on a pool positive sample.

In addition, in current clinical practice, different clinical syndromes, such as cystic fibrosis, β-thalassemia, and Gaucher's disease, are screened independently of each other. The present invention, by contrast, accommodates the simultaneous screening of large numbers of nucleic acid samples from different sources, including different mammals, with a large number of polymers that are complementary to mutations in more than one potential disease-causing gene.

In the same manner, when clinical indicators suggest infection by a foreign agent or microorganism, the present invention provides for simultaneous screening for a large number of potential foreign nucleic acids. Furthermore, particular strains, variants, mutants, and the like of one or more microorganisms can also be distinguished by employing appropriate polymers in the first screening.

The methods of the present invention also make it possible to define potentially novel mutant alleles carried in the nucleic acid of a patient or an invading microorganism, by the use of randomly permuted polymers in phase one or phase two screening. In this embodiment, separation of the bound polymers, followed by sequencing, reveals the precise mutant sequence.

This invention further contemplates a kit for carrying out high-throughput screening of nucleic acid samples according to this invention. The kit will include, in packaged combination, at least the following components: a support, a multiplicity of purine and pyrimidine containing polymers, appropriate labeling components, and enzymes and reagents required for polymer sequence determination.

The following examples are intended to further illustrate the present invention without limiting the invention thereof.

EXAMPLE 1
Preparation of Target DNA
A) Preparation of Sample DNA from Blood

Whole blood samples collected in high glucose ACD Vacutainers™ (yellow top) were centrifuged and the buffy coat collected. The white cells were lysed with two washed of a 10:1 (v/v) mixture of 14 mM $NH_4Cl$ and 1 mM $NaHCO_3$, their nuclei were resuspended in nuclei-lysis buffer (10 mM Tris, pH 8.0, 0.4M NaCl, 2 mM EDTA, 0.5% SDS, 500 μg/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA).

B) Preparation of Sample DNA from Buccal Cells

Buccal cells were collected on a sterile cytology brush (Scientific Products) or female dacron swab (Medical Packaging Corp.) by twirling the brush or swab on the inner cheek for 30 seconds. DNA was prepared as follows, immediately or after storage at room temperature or at 4° C. The brush or swab was immersed in 600 μl of 50 mM NaOH contained in a polypropylene microcentrifuge tube and vortexed. The tube, still containing the brush or swab, was heated at 95° C. for 5 min, after which the brush or swab was carefully removed. The solution containing DNA was then neutralized with 60 μl of 1M Tris, pH 8.0, and vortexed again (Mayall et al., *J.Med.Genet.* 27:658, 1990). The DNA was stored at 40° C.

C) Amplification of Target DNA Prior to Hybridization

DNA from patients with CF was amplified by PCR in a Perkin-Elmer Cetus 9600 Thermocycler. Five primer sets were used to simultaneously amplify relevant regions of exons 4, 10, 20, and 21 of the cystic fibrosis transmembrane conductance regulator (CFTR) gene (Richards et al., *Human Mol.Gen.* 2:159, 1993). The 50 μl PCR reaction mix contained the following components: 0.2–1 μg CF patient DNA, 10 mM Tris pH 8.3, 50 mM KCl, 1.5mM $MgCl_2$, 0.01% (w/v) gelatin, 200 μM of each deoxynucleotide triphosphate, 0.4 μM of each amplification primer, and 2.5 units of Taq polymerase. An initial denaturation was performed by incubation at 94° C. for 20 seconds, followed by 28 cycles of amplification, each consisting of 10 seconds at 94° C., 10 seconds at 55° C., 10 seconds at 74° C, and a final soak at 74° C. for 5 min. Following amplification, 8 μl of the PCR products were electrophoresed in a 2% agarose gel to verify the presence of all five products.

D) Binding of DNA to a Solid Matrix:

8 μl of the amplified DNA solution prepared as in C) were added to 50 μl of a denaturing solution (0.5 mM NaOH, 2.0M NaCl, 25 mM EDTA) and spotted onto nylon membrane filters (INC Biotrans). The DNA was then fixed to the membranes by baking the filters at 80° C. for 15 minutes under vacuum.

EXAMPLE 2
Hybridization with Allele-Specific Oligonucleotides

The oligonucleotides shown in Table 1 represent known cystic fibrosis (CF) alleles.

TABLE 1

| ASO | Sequence (17-mer) | |
|---|---|---|
| Mutant ASO Sequences | | |
| ΔF508M | 5'ACA/CCA/ATG/ATA/TTT/TC 3' | SEQ ID NO:1 |
| G542XM | 5'ATT/CCA/CCT/TCT/CAA/AG 3' | SEQ ID NO:2 |
| G551DM | 5'CTC/GTT/GAT/CTC/CAC/TC 3' | SEQ ID NO:3 |
| R553XM | 5'CTC/ATT/GAC/CTC/CAC/TC 3' | SEQ ID NO:4 |
| W1282XM | 5'CTT/TCC/TTC/ACT/GTT/GC 3' | SEQ ID NO:5 |
| N1303KM | 5'TCA/TAG/GGA/TCC/AAC/TT 3' | SEQ ID NO:6 |

TABLE 1-continued

| ASO | Sequence (17-mer) | |
|---|---|---|
| A1507M | 5'ACA/CCA/AAG/ATA/TTT/TC 3' | SEQ ID NO:7 |
| R117HM | 5'CGA/TAG/AGT/GTT/CCT/CC 3' | SEQ ID NO:8 |
| 621 + 1M | 5'GCA/AGG/AAG/TAT/TAA/CT 3' | SEQ ID NO:9 |
| 5549NM | 5'CTC/GTT/GAC/CTC/CAT/TC 3' | SEQ ID NO:10 |
| R560TM | 5'TAT/TCA/CGT/TGC/TAA/AG 3' | SEQ ID NO:11 |
| 1717 − 1M | 5'GGA/GAT/GTC/TTA/TTA/CC 3' | SEQ ID NO:12 |
| 3849 + 10M | 5'ACT/CAC/CAT/TTT/AAT/AC 3' | SEQ ID NO:13 |
| 3905 + TM | 5'GTA/GTC/TCA/AAA/AAA/GC 3' | SEQ ID. NO:14 |
| R347PM | 5'GTG/ACC/GCC/ATG/GGC/AG 3' | SEQ ID NO:15 |
| 1078dTBM | 5'CAC/CAC/AAG/AAC/CCT/GA 3' | SEQ ID NO:16 |
| 2789 + 5GAM | 5'GGA/ATA/TTC/ACT/TTC/CA 3' | SEQ ID NO:17 |
| 3849 + 4CM | 5'GCA/GTG/TTC/AAA/TCC/CA 3' | SEQ ID NO:18 |
| 711 + 1GTM | 5'CAT/AAT/TCA/TCA/AAT/TT 3' | SEQ ID NO:19 |
| R1162XM | 5'CTC/AGC/TCA/CAG/ATC/GC 3' | SEQ ID NO:20 |
| 1898 + 1GAM | 5'CAT/ATC/TTT/CAA/ATA/TT 3' | SEQ ID NO:21 |
| 3659dCM | 5'CTT/GTA/GGT/TTA/CCT/TC 3' | SEQ ID NO:22 |
| G85EM | 5'GAT/TTC/ATA/GAA/CAT/AA 3' | SEQ ID NO:23 |
| 2184dAM | 5'GAT/TGC/TTT/TTG/TTT/CT 3' | SEQ ID NO:24 |
| A455EM | 5'AAC/CTC/CAA/CAA/CTG/TC 3' | SEQ ID NO:25 |
| R334WM | 5'TTC/CAG/AGG/ATG/ATT/CC 3' | SEQ ID NO:26 |
| Y122XBM | 5'AGT/TAA/ATC/GCG/ATA/GA 3' | SEQ ID NO:27 |
| 5549RBM | 5'TCC/CCT/CAG/TGT/GAT/TC 3' | SEQ ID NO:28 |
| Q493XM | 5'ACT/AAG/AAC/AGA/ATG/AA 3' | SEQ ID NO:29 |
| VS2OFM | 5'GAT/GAA/GCT/TCT/GTA/TC 3' | SEQ ID NO:30 |
| Y1092XM | 5'ACA/GTT/ACA/AGA/ACC/AG 3' | SEQ ID NO:31 |
| R347HM | 5'GTG/ACC/GCC/ATG/TGC/AG 3' | SEQ ID NO:32 |
| Normal ASO Sequences | | |
| ΔF5O8N | 5'CAT/AGG/AAA/CAC/CAA/AG 3' | SEQ ID NO:33 |
| G542XN | 5'ATT/CCA/CCT/TCT/CCA/AG 3' | SEQ ID NO:34 |
| G551DN | 5'CTC/GTT/GAC/CTC/CAC/TC 3' | SEQ ID NO:35 |
| R553XN | See GS51DN sequence | |
| W1282XN | 5'CTT/TCC/TCC/ACT/GTT/GC 3' | SEQ ID NO:36 |
| N1303KN | 5'TCA/TAG/GGA/TCC/AAG/TT 3' | SEQ ID NO:37 |
| Δ507N | 5'ACA/CCA/AAG/ATG/ATA/Tr 3' | SEQ ID NO:38 |
| Ri17HN | 5'CGA/TAG/AGC/GTT/CCT/CC 3' | SEQ ID NO:39 |
| 621 + 1N | 5'GCA/AGG/AAG/TAT/TAC/CT 3' | SEQ ID NO:40 |
| 5549NN | See G5S1DN sequence | |
| R560TN | 5'TAT/TCA/CCT/TGC/TAA/AG 3' | SEQ ID NO:41 |
| 1717 − 1N | 5'GGA/GAT/GTC/CTA/TTA/CC 3' | SEQ ID NO:42 |
| 3849 + 10N | 5'ACT/CGC/CAT/TTT/AAT/AC 3' | SEQ ID NO:43 |
| 3905 + TN | 5'GTA/GTC/TCA/AAA/AAG/CT 3' | SEQ ID NO:44 |
| R347PN | 5'GTG/ACC/GCC/ATG/CGC/AG 3' | SEQ ID NO:45 |
| 10O78dTBN | 5'CAC/CAC/AAA/GAA/CCC/rG 3' | SEQ ID NO:46 |
| 2789 + SGAN | 5'GGA/ATA/CTC/ACT/TTC/CA 3' | SEQ ID NO:47 |
| 3849 + 4CN | 5'GCA/GTG/TTC/AAA/TCT/CA 3' | SEQ ID NO:48 |
| 711 + 1GTN | 5'CAT/ACT/TCA/TCA/AAT/TT 3' | SEQ ID NO:49 |
| R1162XN | 5'CTC/GGC/TCA/CAG/ATC/GC 3' | SEQ ID NO:50 |
| 1898 + 1GAN | 5'CAT/ACC/TTT/CAA/ATA/TT 3' | SEQ ID NO:51 |
| 3659dCN | 5'CTT/GGT/AGG/TTT/ACC/TT 3' | SEQ ID NO:52 |
| G85EN | 5'GAT/TCC/ATA/GAA/CAT/AA 3' | SEQ ID NO:53 |
| 2184dAN | 5'GAT/TGT/TTT/TTT/GTT/TC 3' | SEQ ID NO:54 |
| A455EN | 5'AAC/CQC/CAA/CAA/CTG/TC 3' | SEQ ID NO:55 |
| R334WN | 5'TTC/CGG/AGG/ATG/ATT/CC 3' | SEQ ID NO:56 |
| Y122XBN | 5'AGA/TAA/ATC/GCG/ATA/GA 3' | SEQ ID NO:57 |
| S549RBN | 5'TCC/ACT/CAG/TGT/GAT/TC 3' | SEQ ID NO:53 |
| Q493XN | 5'ACT/GAG/AAC/AGA/ATG/AA 3' | SEQ ID NO:59 |
| VS20FN | 5'GAT/GAC/GCT/TCT/GTA/TC 3' | SEQ ID NO:60 |
| Y1092XN | 5'ACA/GGT/ACA/AGA/ACC/AG 3' | SEQ ID NO:61 |
| R347HN | See R347PN sequence | |

A) Hybridizations:

The oligonucleotides shown in Table 1 were chemically synthesized using an automated synthesizer, and were radio-labeled with $^{32}$p with polynucleotide kinase, using methods that are standard in the art.

Hybridizations were carried out in plastic bags containing the filters prepared as in Example 1D above, to which pooled radiolabeled ASOs were added in a TMAC hybridization buffer (3.0M TMAC, 0.6% SDS, 1 mM EDTA, 10 mM sodium phosphate pH 6.8, 5×Denhardt's Solution, and 40 μg/ml yeast RNA). ASO concentrations in the pools ranged from 0.03 to 0.15 pmol/ml hybridization solution.

Hybridizations were allowed to proceed overnight at 52° C., with agitation. The membranes were then removed from the bags and washed for 20 min at room temperature with wash buffer (3.0M TMAC, 0.6% SDS, 1 mM EDTA, 10 mM sodium phosphate pH 6.8), followed by a second wash in the same buffer for 20 min at 52° C. The membranes were then dried and exposed to Kodak X-OMAT film.

Figure 1:
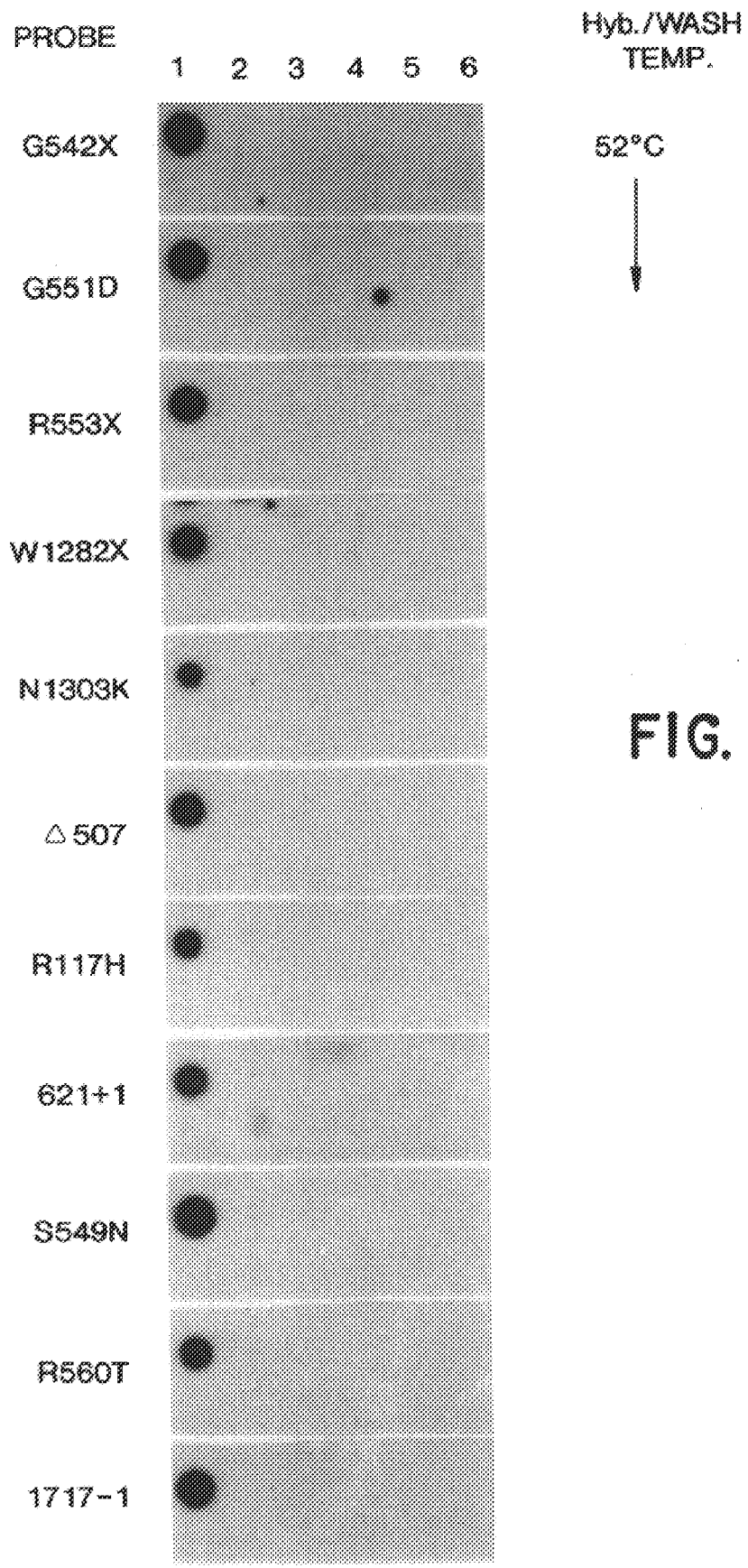
FIG. 1 shows autoradiographic results obtained from hybridizing multiple identical filters containing human genomic DNA with $^{32}$P-labeled ASOs specific for different alleles of the cystic fibrosis transmembrane regulator (CFTR) gene. The ASOs used in each hybridization are identified on the left of each filter. Lane 1 in each case contains DNA carrying the mutant sequence complementary to each ASO; lanes 2–6 contain wild-type "normal" sequences.

B) Results:

The specificity of hybridization using the conditions described in A) was evaluated by probing amplified samples from individuals of known genotype with 11 of the ASOs described above (Table 1). The results are shown in FIG. 1. Each ASO hybridized specifically only to samples carrying the complementary mutant sequence (lane 1 in each case) and not to samples not containing that sequence (as in lanes 2–6, containing wild-type "normal" sequences).

Figure 3:
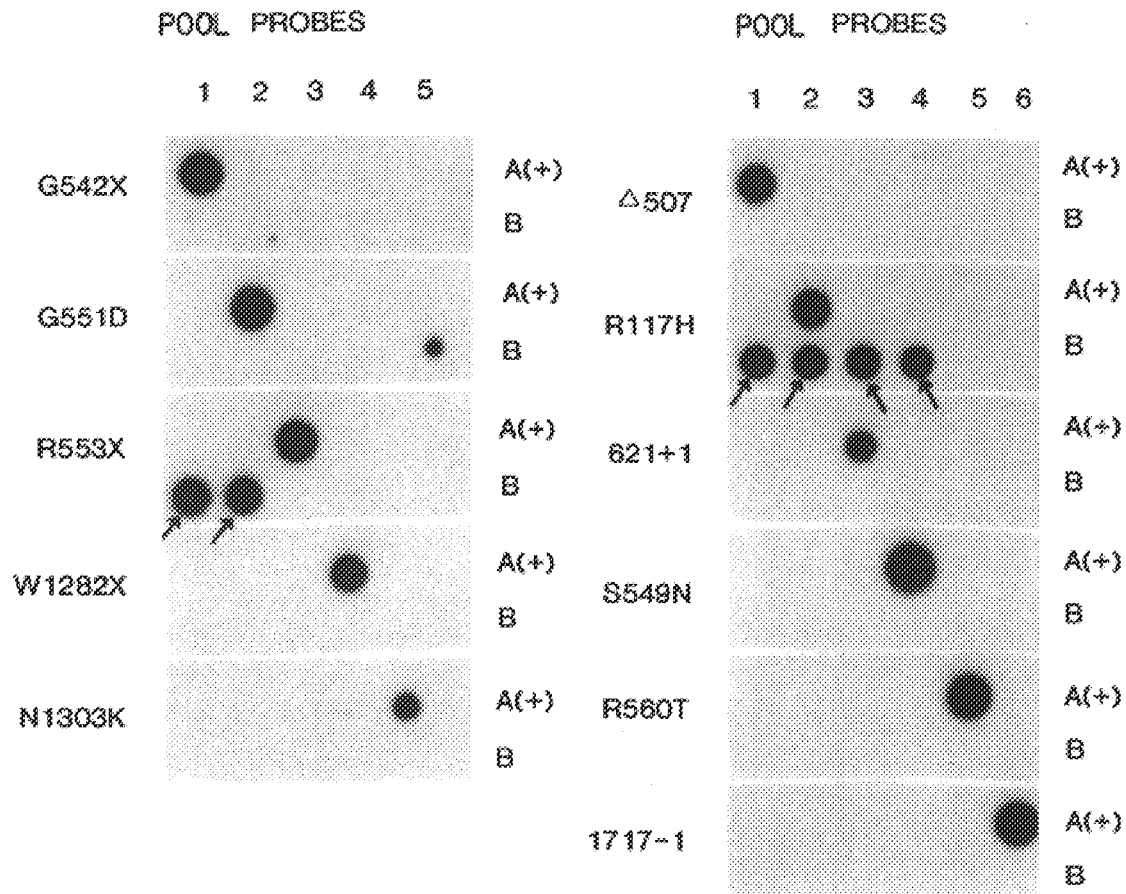
FIG. 3 shows the identification of specific mutations in pool-positive samples identified in FIG. 1. The top row of each filter contains positive control samples for ASOs in pool 1 and pool 2 as indicated. Pool 1, lane 1, G542X; lane 2, G551D; lane 3, R553X; lane 4, W1282X; lane 5, N1303K. Pool 2, lane 1, Δ507; lane 2, R117H; lane 3, 621+1 G→T; lane 4, S549N; lane 5, R560T; lane 6, 1717-1 GΔA. Row B contains pool-1 or pool-2 positive patient samples. Pool 1, lanes 1 and 2 contain sample 4, lanes D and E from FIG. 1.

When pools of ASOs were used, identical results were observed (FIG. 2). In this experiment, four separate hybridizations were performed, containing ASOs included in Table 1. In this case, the samples spotted in lanes 1–12, rows B and C, were negative for all mutations (bottom three panels), but were positive for the wild-type Δ508 sequence (top panel). By contrast, the sample spotted in lane 6, rows D and E, was positive for the Δ508 mutation and negative for the wild-type sequence, indicating that this patient was homozygous for the Δ508 allele. Similarly, the sample in lane 4, rows D and E, was pool-1 positive, while the samples in lanes 3 and 5, rows D and E, were pool-2 positive. Subsequent individual hybridizations of the latter samples with each probe in pool 1 and pool 2 verified that the pool-positive hybridizations were in fact due to hybridization with a single member of the pool (FIG. 3). That is, the sample from lane 4, rows D and E of FIG. 2 was shown to hybridize specifically with the R553X ASO, while the samples in lanes 3 and 5, D and E of FIG. 2 hybridized specifically with the R117H ASO.

EXAMPLE 3
Separation of Bound ASOs

The present invention encompasses a method for hybridizing a large number of potential polymers to a patient's DNA in a single hybridization reaction. In a subsequent step, the polymers that have bound to the target DNA are separated and identified, with or without prior amplification.

Pool-positive samples from hybridizations performed as in Example 2 are treated as follows: Positive spots are excised in the form of discs from the nylon membrane using a standard single hole paper punch. Each of the excised membrane discs is then placed in separate 31.5 ml microcentrifuge tubes containing 100 μl of sterile water, and the tubes are incubated at 100° C. for 15 minutes (FIG. 4).

EXAMPLE 4
Design of Complementary Oligonucleotides for Identification of Bound ASOs In practicing the present invention, the sequence of separated polymers may be determined directly using chemical sequencing. Alternatively, separated polymers may be used in conjunction with complementary oligonucleotides that contain other sequences in addition to sequences complementary to the polymers. In these cases, the separated polymers serve as primers to form extension products that contain the additional sequences, and the extension products are subjected to DNA sequencing.

Following are several embodiments of complementary oligonucleotides that contain the complement of the R334W CF mutation-specific ASO (Table 1).
Version 1: Separated ASO as sequencing primer 3' A A G G T C T C C T A C T A A G G - TCTCGCTTCGTTTCATCTCATCTCG 5' SEQ ID NO:62 ASO complement "Tag"

In this embodiment, the separated ASO is incubated with the complementary oligonucleotide in a Sanger sequencing reaction, and the sequence is determined directly.
Version 2: Cycle sequencing of separated ASO 3 ' A A G G T C T C C T A C T A A G G - TCTCGCTTCGTTTCATCTCATCTCG-ASO complement "Tag" ATCGATCGATCGATCGATCGATCG 5' SEQ ID NO:63

Universal Primer Sequence

In this embodiment, the separated ASO serves as a primer for a single extension reaction. The extension product is then subjected to cycle sequencing, using the universal primer to prime the sequencing reaction (see Example 5 below).

Version 3: Amplification of complementary oligonucleotide for Sanger sequencing 3' AAGGTCTCCTACTAAGG-CGCCAGGGTTTTCCCAGTCA-ASO complement "sequencing target" TCTCGCTTCGTTCATCTCATCTCG-ATCGATCGATCGATCGATCGATCGA 5' "Tag" Universal Primer Sequence SEQ ID NO:64

In this embodiment, the separated ASO serves as a primer for a single extension reaction. The extension product is then amplified using the universal primer sequence and the separated ASO as amplification primers. Finally, the amplification products are subjected to Sanger sequencing using as a primer an oligonucleotide corresponding to the sequencing target (see Example 6 below).

EXAMPLE 5
Cycle Sequencing of Separated ASOs
A) Extension Reaction

A separated mutation-specific oligonucleotide, designated R334W, having the sequence 5'-TTCCAGAGGATGATTCC-3' SEQ ID NO:65 is added to a reaction mix containing reaction components necessary for a single round of extension. The complementary oligonucleotide (Version 2 in Example 4 above) contains a universal primer sequence at its 5' end, separated by 25–30 bases from the complement to R334W at its 3' end. The extension reaction contains the following components:

25 μl separated ASO
5 μl 10X buffer (0.5 mM Tris-HCl pH 7.5, 0.1M MgCl$_2$, 10 mM dithiothreitol) 1 μl dNTPs (2.5 mM each) 1 μl complementary oligonucleotides (100 ng/ml) 13 μl H$_2$O 1 μl Klenow fragment of DNA polymerase (10 U/μl)

The reaction is allowed to proceed at room temperature for 30 minutes.
B) Cycle Sequencing:

An aliquot of the above reaction is added to a PCR reaction mix containing two or more dideoxynucleotide analogues (ddNTPs), according to the following protocol:

10 μl extension products
5 μl 10× buffer (300 mM Tris-HCl pH 9.0, 50 mM MgCl$_2$, 300 mM KCl)
5 μl universal primer (1 pmole)
10 μl 2 mM ddATP, ddCTP, ddGTP; 100 μM dATP, dCTP, dGTP, dTTP
19 μl H$_2$O
1 μl Taq polymerase (10 U/μl)

30 cycles of amplification are performed, creating a heterogeneous population of random termination products that terminate at positions corresponding to nucleotides downstream of the universal primer sequence. The products of the PCR reaction are then separated in a denaturing polyacrylamide gel, creating a banding pattern specific for this ASO. The electrophoretic pattern is analyzed by autoradiography or fluorimetry.

EXAMPLE 6
Amplification and Sequencing of Complementary Oligonucleotides

A separated mutation-specific oligonucleotide, designated R334W, having the sequence 5'-TTCCAGAGGATGATTCC-3'(SEQ ID NO:65) is added to a reaction mix containing reaction components for extension as in Example 5, Step A. The complementary oligonucleotide (Version 3 in Example 4 above) contains a universal primer sequence at its 5' end, a "tag" sequence, "sequencing target" sequence, followed by the complement to R334W at its 3' end. Following the extension reaction, an aliquot of the reaction is added to an amplification mixture containing the following components:

3 µl extension products

1 µl universal amplification primer (10 µM)

2.5 µl dATP, dTTP, dCTP, dGTP (2 mM each)

2 µl 40 mM $MgCl_2$

5 µl 100 mM Tris-HCl pH 8.3, 500 mM KCl 26.4 µl $H_2O$ 0.1 µl Amphitaq DNA polymerase (5 U/ml).

The reaction is then subjected to 35 cycles of amplification, using a GeneAmp PCR System 9600 Thermocycler. 2 µl of the amplification products are then removed and subjected to Sanger sequencing, using the Sanger sequencing primer.

EXAMPLE 7

RNA as a Target Nucleic Acid

In a similar manner to Example 1, which describes DNA as a target nucleic acid, RNA may also be used as a target nucleic acid.

A) Preparation of RNA from Target Cells

Cells are collected by centrifugation, and the supernatant is removed. The cell pellet is resuspended in cold lysis buffer (140 mM NaCl, 1.5 mM $MgCl_2$, 10 mM Tris-Cl, pH 8.5, 0.5% NP-40, and RNasin® (from Promega Inc.). Cellular debris is pelleted by centrifugation for 5 minutes at 4° C. at 5000×g. The supernatant is transferred to a fresh tube and the EDTA concentration brought to 10 mM. Proteins are removed by extraction with phenol-chloroform saturated with aqueous Tris 10 mM, pH 8.5. The aqueous phase is precipitated with sodium acetate at pH 5.2 and 2.5 volumes of ice cold ethanol overnight at 10° C. RNA is collected by centrifugation at 10,000×g at 4° C. for 30 minutes.

B) Conversion of RNA to cDNA Before Amplification

RNA may be used directly in the manner of the present invention, or converted to amplified DNA via a reverse transcription PCR protocol. According to this protocol, 1 µg of RNA is mixed with 100 pmol of appropriate primers, 1 mM NTPs, 1 U/µl RNasin® in 20 µl of PCR buffer (50 mM KCl, 20 mM Tris, pH 8.4, 2.5 mM $MgCl_2$) and 200 U of reverse transcriptase. The mixture is incubated at 23° C. for 10 minutes, then 42° C. for 45 minutes, then 95° C. for 5 minutes, and then quick chilled. Conventional PCR protocols, similar to those described in Example 1, may be used to amplify the resultant cDNA.

EXAMPLE 8

Unique Probe Identifiers

Instead of determining the identity of the separated polymer by using chemical or enzymatic sequencing reactions, it is also possible to label each probe polymer with a unique identifier moiety which can be detected directly or indirectly. The following description merely demonstrates examples of the full range of unique probe identifiers that one of skill would readily understand to have use in the present invention.

A) Fluorescent Labels

Oligonucleotides are hybridized to immobilized nucleic acid targets in a similar manner to Example 2, except that each ASO in the pool is labeled with a unique fluorescent probe instead of $^{32}P$. For example, ASOs ΔF508M, G542XM, G551DM and R553XM are labeled with Texas Red, tetramethylrhodamine, fluorescein, Cy3, respectively. Similar to Example 3, bound ASOs can be detected, as having been bound, prior to separation. In this Example, ASO binding is detected by fluorescence of the conjugated label either visually or by any number of automated methods. After separation, the ASO can be positively identified by measuring emission wavelength in response to fluor excitation.

B) Molecular Weight Labels

Oligonucleotides are hybridized to immobilized nucleic acid targets in a similar manner to Example 2, except that each ASO in the pool is additionally labeled with a unique molecular weight modifying entity. For example, the four ASOs described in Example 8 A) are each derivatized with a 5' oligomeric hexaethyleneoxide (HEO) tail of differing length. ASOs ΔF508M, G542XM, G551DM and R53XM can be labeled with lengths of 5, 10, 15 and 20 HEO units each. The tails are added using standard DNA synthesis protocols such as described in Nucleic Acid Res. 22(21): 4527. The HEO tail does not participate in hydrogen bonding but does give a unique molecular weight to each ASO. The ASO can be identified without further modification by distinguishing the separated ASOs by molecular weight, using any number of commonly recognized methods, such as gel or capillary electrophoresis.

C) An Alternative Molecular Weight Labeling Method

An additional method of utilizing molecular weight identification of the hybridizing polymer is to add an additional number of nucleotides to the polymer enzymatically after separation from target nucleic acid. One preferred form of this method is to collect the separated polymer, after hybridization to the immobilized nucleic acid target, into a tube containing oligonucleotides, each of which are complementary to one member of the polymer pool used to probe the target nucleic acid. In addition to a portion that is complementary to the polymer, the oligonucleotide also contains an additional sequence, the length of which is unique for that oligonucleotide. When the polymer and oligonucleotide hybridize, the polymer can subsequently be used as a primer to enzymatically extend the polymer to the full length of the complimentary oligonucleotide. During this process, a direct or indirect label, as described above, may be incorporated by a labeled nucleotide triphosphate. The extended oligonucleotide can be identified by determining the relative molecular weight of the labeled product by any number of established methods, such as gel or capillary electrophoresis.

I claim:

1. A method for screening nucleic acid samples to identify one or more genetic alterations of interest in one or more target sequences present in said samples, comprising the steps of:

(i) immobilizing a plurality of said samples on a support;

(ii) simultaneously hybridizing said samples with a pool of polymer probes wherein said pool comprises individual purine and pyrimidine containing polymers, each polymer complementary to and specific for one of said one or more genetic alterations of interest suspected to be present in said target sequences;

(iii) removing the purine and pyrimidine containing polymers that do not hybridize to said samples;

(iv) detecting the presence of polymer:sample hybrids;

(v) individually separating said purine and pyrimidine containing polymers hybridized to said samples; and (vi) identifying said separated purine and pyrimidine containing polymers wherein the identification of said separated purine and pyrimidine containing polymers identifies the nucleic acid sequence of said genetic alteration(s).

2. A method for identifying one or more target sequences of interest present in a nucleic acid sample, comprising the steps of:

(i) immobilizing a plurality of nucleic acid samples on a support;

(ii) simultaneously hybridizing said samples with a pool of polymer probes wherein said pool comprises individual purine and pyrimidine containing polymers, each polymer complementary to and specific for one of said one or more target sequences of interest suspected to be present in said samples;

(iii) removing the purine and pyrimidine containing polymers that do not hybridize to said samples;

(iv) detecting polymer:sample hybrids;

(v) individually separating said polymers hybridized to each of said samples; and (vi) determining the sequence of said individually separated purine and pyrimidine containing polymers wherein the sequence identifies the nucleic acid sequence of said one or more targets present in said sample.

3. The method of claim 2, wherein the nucleic acid sample is obtained from a patient.

4. The method of claim 2, wherein the target sequence is selected from the group consisting of viral, bacterial, fungal, and protozoal nucleic acid sequences.

5. A method for identifying one or more randomly permuted alteration of interest in a target sequence present in a nucleic acid sample, comprising the steps of:

(i) immobilizing a plurality of nucleic acid samples on a support;

(ii) simultaneously hybridizing said samples with a pool of polymer probes wherein said pool comprises individual purine and pyrimidine containing polymers, each polymer complementary to and specific for one of said one or more randomly permuted alterations of interest suspected to be present in said target sequence;

(iii) removing the purine and pyrimidine containing polymers that do not hybridize to said samples (iv) detecting the presence of polymer:sample hybrids;

(v) individually separating each of said purine and pyrimidine containing polymers hybridized to each of said samples; and (vi) identifying said separated purine and pyrimidine containing polymers wherein the identification of said separated purine and pyrimidine containing polymers identifies said randomly permuted alteration (s) in said target sequence.

6. The method of claim 1, wherein said pool of polymer probes is divided into two or more pools, each pool comprising individual purine and pyrimidine containing polymers, each polymer complementary to and specific for one of a group of alterations comprising genetic alterations selected from the one or more genetic alterations of interest suspected to be present in said target sequence and wherein each pool is separately hybridized to said sample(s).

7. The method as in claims 1, 2 or 5, wherein in the immobilizing step, the support is a solid phase support or a semi-solid phase support.

8. The method as in claims 1, or 5, wherein said identifying step includes determining the sequence of said separated purine and pyrimidine containing polymers.

9. The method of claim 1 wherein the alterations comprise nucleotide insertions, deletions, or substitutions.

10. The method of claim 1 wherein the nucleic acid samples are suspected of containing one or more genetic alterations.

11. The method of claim 10, wherein the genetic alteration (s) is associated with a genetic disease selected from the group consisting of cystic fibrosis, beta-thalassemia, Tay-Sachs disease, sickle cell anemia, and Gaucher's disease.

12. The method of claim 1, wherein said purine and pyrimidine containing polymers are from about 16 to about 25 nucleotides in length.

13. The method of claim 1, wherein the target sequence is amplified prior to the immobilizing step.

14. The method of claim 13, wherein the amplified sequence is from about 80 bp to about 30 kbp in length.

15. The method of claim 7, wherein the solid phase support is selected from the group consisting of nitrocellulose filter, nylon filter, glass beads, and plastic.

16. The method of claim 7, wherein the semi-solid phase support is selected from the group consisting of a polymer gel, and agarose.

17. The method of claim 1, wherein said purine and pyrimidine containing polymers are of equivalent length, and the hybridizing step is performed in the presence of an effective concentration of an agent that eliminates disparities in the melting temperatures of hybrids formed between said purine and pyrimidine containing polymers and said nucleic acid samples.

18. The method of claim 17, wherein the agent is a quaternary ammonium salt.

19. The method of claim 18, wherein the quaternary ammonium salt is tetramethyl ammonium chloride.

20. The method of claim 8, wherein the sequence is determined by chemical sequencing.

21. The method of claim 1, wherein the nucleic acid samples are derived from more than one mammal.

22. The method of claim 1, wherein the identifying step comprises:

(a) contacting said separated purine and pyrimidine containing polymers with a multiplicity of complementary oligonucleotides comprising (i) sequences complementary to said polymers and (ii) additional predetermined colinear sequences;

(b) performing enzymatic sequencing, wherein said polymers serve as primers and the complementary oligonucleotides serve as templates for the enzymatic sequencing; and (c) identifying the predetermined colinear sequences as an indicator of the presence of said polymers.

23. The method of claim 1, wherein the identifying step comprises:
(a) contacting said separated purine and pyrimidine containing polymers with a multiplicity of complementary oligonucleotides comprising (i) sequences complementary to said polymers and (ii) additional predetermined colinear sequences;
(b) performing a single extension reaction, wherein said polymers serve as primers and the complementary oligonucleotides serve as templates for the extension reaction;
(c) performing enzymatic sequencing of the products of the extension reaction; and
(d) identifying the predetermined colinear sequences as an indicator of the presence of said polymers.

24. The method of claim 1, wherein said purine and pyrimidine polymers are each provided with a molecular weight modifying entity having a unique molecular weight.

25. The method of claim 1, wherein said purine and pyrimidine polymers are each provided with a detectable label.

* * * * *

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:

(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:1:

ACACCAATGA TATTTTC                                                17

(2) INFORMATION FOR SEQ ID NO:2:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:2:

ATTCCACCTT CTCAAAG                                                17

(2) INFORMATION FOR SEQ ID NO:3:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:3:

CTCGTTGATC TCCACTC                                                17

(2) INFORMATION FOR SEQ ID NO:4:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:4:

CTCATTGACC TCCACTC                                                17

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:5:

CTTTCCTTCA CTGTTGC                                                17

(2) INFORMATION FOR SEQ ID NO:6:

(i) SEQUENCE CHARACTERISTICS:

(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:6:

TCATAGGGAT CCAACTT 17

(2) INFORMATION FOR SEQ ID NO:7:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:7:

ACACCAAAGA TATTTTC 17

(2) INFORMATION FOR SEQ ID NO:8:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:8:

CGATAGAGTG TTCCTCC 17

(2) INFORMATION FOR SEQ ID NO:9:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:9:

GCAAGGAAGT ATTAACT 17

(2) INFORMATION FOR SEQ ID NO:10:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:10:

CTCGTTGACC TCCATTC 17

(2) INFORMATION FOR SEQ ID NO:11:

(i) SEQUENCE CHARACTERISTICS:

(A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:11:

TATTCACGTT GCTAAAG                               17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:12:

GGAGATGTCT TATTACC                               17

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:13:

ACTCACCATT TTAATAC                               17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:14:

GTAGTCTCAA AAAAAGC                               17

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:15:

GTGACCGCCA TGGGCAG                               17

(2) INFORMATION FOR SEQ ID NO:16:

(i) SEQUENCE CHARACTERISTICS:

(A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotide"

(x i) SEQUENCE DESCRIPTION: SEQ ID NO:16:

CACCACAAGA ACCCTGA                                                                                 17

(2) INFORMATION FOR SEQ ID NO:17:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotide"

(x i) SEQUENCE DESCRIPTION: SEQ ID NO:17:

GGAATATTCA CTTTCCA                                                                                 17

(2) INFORMATION FOR SEQ ID NO:18:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotide"

(x i) SEQUENCE DESCRIPTION: SEQ ID NO:18:

GCAGTGTTCA AATCCCA                                                                                 17

(2) INFORMATION FOR SEQ ID NO:19:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotide"

(x i) SEQUENCE DESCRIPTION: SEQ ID NO:19:

CATAATTCAT CAAATTT                                                                                 17

(2) INFORMATION FOR SEQ ID NO:20:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotides"

(x i) SEQUENCE DESCRIPTION: SEQ ID NO:20:

CTCAGCTCAC AGATCGC                                                                                 17

(2) INFORMATION FOR SEQ ID NO:21:

(i) SEQUENCE CHARACTERISTICS:

(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:21:

CATATCTTTC AAATATT 17

(2) INFORMATION FOR SEQ ID NO:22:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:22:

CTTGTAGGTT TACCTTC 17

(2) INFORMATION FOR SEQ ID NO:23:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:23:

GATTTCATAG AACATAA 17

(2) INFORMATION FOR SEQ ID NO:24:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:24:

GATTGCTTTT TGTTTCT 17

(2) INFORMATION FOR SEQ ID NO:25:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:25:

AACCTCCAAC AACTGTC 17

(2) INFORMATION FOR SEQ ID NO:26:

(i) SEQUENCE CHARACTERISTICS:

(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:26:

TTCCAGAGGA TGATTCC  17

(2) INFORMATION FOR SEQ ID NO:27:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:27:

AGTTAAATCG CGATAGA  17

(2) INFORMATION FOR SEQ ID NO:28:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:28:

TCCCCTCAGT GTGATTC  17

(2) INFORMATION FOR SEQ ID NO:29:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:29:

ACTAAGAACA GAATGAA  17

(2) INFORMATION FOR SEQ ID NO:30:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:30:

GATGAAGCTT CTGTATC  17

(2) INFORMATION FOR SEQ ID NO:31:

(i) SEQUENCE CHARACTERISTICS:

(A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotides"

(x i) SEQUENCE DESCRIPTION: SEQ ID NO:31:

ACAGTTACAA GAACCAG                                                                                  17

(2) INFORMATION FOR SEQ ID NO:32:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotides"

(x i) SEQUENCE DESCRIPTION: SEQ ID NO:32:

GTGACCGCCA TGTGCAG                                                                                  17

(2) INFORMATION FOR SEQ ID NO:33:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotides"

(x i) SEQUENCE DESCRIPTION: SEQ ID NO:33:

CATAGGAAAC ACCAAAG                                                                                  17

(2) INFORMATION FOR SEQ ID NO:34:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotides"

(x i) SEQUENCE DESCRIPTION: SEQ ID NO:34:

ATTCCACCTT CTCCAAG                                                                                  17

(2) INFORMATION FOR SEQ ID NO:35:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "Oligonucleotides"

(x i) SEQUENCE DESCRIPTION: SEQ ID NO:35:

CTCGTTGACC TCCACTC                                                                                  17

(2) INFORMATION FOR SEQ ID NO:36:

(i) SEQUENCE CHARACTERISTICS:

(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:36:

CTTTCCTCCA CTGTTGC 17

(2) INFORMATION FOR SEQ ID NO:37:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:37:

TCATAGGGAT CCAAGTT 17

(2) INFORMATION FOR SEQ ID NO:38:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:38:

ACACCAAAGA TGATATR 17

(2) INFORMATION FOR SEQ ID NO:39:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:39:

CGATAGAGCG TTCCTCC 17

(2) INFORMATION FOR SEQ ID NO:40:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:40:

GCAAGGAAGT ATTACCT 17

(2) INFORMATION FOR SEQ ID NO:41:

(i) SEQUENCE CHARACTERISTICS:

(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:41:

TATTCACCTT GCTAAAG 17

(2) INFORMATION FOR SEQ ID NO:42:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:42:

GGAGATGTCC TATTACC 17

(2) INFORMATION FOR SEQ ID NO:43:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:43:

ACTCGCCATT TTAATAC 17

(2) INFORMATION FOR SEQ ID NO:44:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:44:

GTAGTCTCAA AAAAGCT 17

(2) INFORMATION FOR SEQ ID NO:45:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:45:

GTGACCGCCA TGCGCAG 17

(2) INFORMATION FOR SEQ ID NO:46:

(i) SEQUENCE CHARACTERISTICS:

( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:46:

CACCACAAAG AACCCRG 17

( 2 ) INFORMATION FOR SEQ ID NO:47:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:47:

GGAATACTCA CTTTCCA 17

( 2 ) INFORMATION FOR SEQ ID NO:48:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:48:

GCAGTGTTCA AATCTCA 17

( 2 ) INFORMATION FOR SEQ ID NO:49:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:49:

CATACTTCAT CAAATTT 17

( 2 ) INFORMATION FOR SEQ ID NO:50:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotides"

( x i ) SEQUENCE DESCRIPTION: SEQ ID NO:50:

CTCGGCTCAC AGATCGC 17

( 2 ) INFORMATION FOR SEQ ID NO:51:

( i ) SEQUENCE CHARACTERISTICS:

(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:51:

CATACCTTTC AAATATT 17

(2) INFORMATION FOR SEQ ID NO:52:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:52:

CTTGGTAGGT TTACCTT 17

(2) INFORMATION FOR SEQ ID NO:53:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:53:

GATTCCATAG AACATAA 17

(2) INFORMATION FOR SEQ ID NO:54:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:54:

GATTGTTTTT TTGTTTC 17

(2) INFORMATION FOR SEQ ID NO:55:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotides"

(x i) SEQUENCE DESCRIPTION: SEQ ID NO:55:

AACCGCCAAC AACTGTC 17

(2) INFORMATION FOR SEQ ID NO:56:

(i) SEQUENCE CHARACTERISTICS:

(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:56:

TTCCGGAGGA TGATTCC 17

(2) INFORMATION FOR SEQ ID NO:57:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:57:

AGATAAATCG CGATAGA 17

(2) INFORMATION FOR SEQ ID NO:58:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:58:

TCCACTCAGT GTGATTC 17

(2) INFORMATION FOR SEQ ID NO:59:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:59:

ACTGAGAACA GAATGAA 17

(2) INFORMATION FOR SEQ ID NO:60:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:60:

GATGACGCTT CTGTATC 17

(2) INFORMATION FOR SEQ ID NO:61:

(i) SEQUENCE CHARACTERISTICS:

(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:61:

ACAGGTACAA GAACCAG 17

(2) INFORMATION FOR SEQ ID NO:62:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:62:

AAGTCTCCT ACTAAGGTCT CGCTTCGTTT CATCTCATCT CG 42

(2) INFORMATION FOR SEQ ID NO:63:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:63:

AAGGTCTCCT ACTAAGGTCT CGCTTGCTTT CATCTCATCT CGATCGATCG ATCGATCGAT 60

CGATCG 66

(2) INFORMATION FOR SEQ ID NO:64:

(i) SEQUENCE CHARACTERISTICS:
(A) LENGTH: 86 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:64:

AAGGTCTCCT ACTAAGGCGC CAGGGTTTTC CCAGTCATCT CGCTTCGTTC ATCTCATCTC 60

GATCGATCGA TCGATCGATC GATCGA 86

(2) INFORMATION FOR SEQ ID NO:65:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotides"

(xi) SEQUENCE DESCRIPTION: SEQ ID NO:65:

TTCCAGAGGA TGATTCC 17